United States Patent
Lellouche et al.

(10) Patent No.: US 9,364,623 B2
(45) Date of Patent: Jun. 14, 2016

(54) METHOD AND DEVICE FOR ADMINISTERING OXYGEN TO A PATIENT AND MONITORING THE PATIENT

(75) Inventors: Francois Lellouche, Lac Beauport (CA); Erwan L'Her, Brest (FR)

(73) Assignees: Université Laval, Quebec (CA); Université de Bretagne Occidentale, Brest (FR)

( * ) Notice: Subject to any disclaimer, the term of this patent is extended or adjusted under 35 U.S.C. 154(b) by 443 days.

(21) Appl. No.: 12/837,259

(22) Filed: Jul. 15, 2010

(65) Prior Publication Data

US 2011/0067697 A1    Mar. 24, 2011

Related U.S. Application Data

(60) Provisional application No. 61/213,787, filed on Jul. 15, 2009.

(51) Int. Cl.
*A61M 16/00* (2006.01)
*A61M 16/10* (2006.01)
*A61M 16/12* (2006.01)

(52) U.S. Cl.
CPC ............... *A61M 16/00* (2013.01); *A61M 16/10* (2013.01); *A61M 16/12* (2013.01); *A61M 2016/0027* (2013.01); *A61M 2202/0208* (2013.01); *A61M 2230/04* (2013.01); *A61M 2230/205* (2013.01); *A61M 2230/42* (2013.01); *A61M 2230/432* (2013.01)

(58) Field of Classification Search
CPC ...... A61B 5/0488; A61B 5/087; A61B 5/091; A61B 5/4821; A61B 5/4836; A61M 16/00; A61M 16/10; A61M 16/12; A61M 16/0051; A61M 2202/0208; A61M 2230/60; A61M 2230/005; A61M 2230/08; A61M 2230/205; A61M 2230/432; A61M 2016/0027; A61M 2230/04; A61M 2230/42
USPC ............ 128/204.18, 204.21, 204.22, 204.23, 128/204.26, 205.11, 898, 203.12–203.14, 128/205.23–205.24
See application file for complete search history.

(56) References Cited

U.S. PATENT DOCUMENTS

| | | |
|---|---|---|
| 2,414,747 A | 1/1947 | Kirschbaum |
| 4,889,116 A | 12/1989 | Taube |
| 5,072,737 A | 12/1991 | Goulding |

(Continued)

FOREIGN PATENT DOCUMENTS

| | | |
|---|---|---|
| CA | 2278053 | 3/2010 |
| WO | 0045883 | 8/2000 |
| WO | 2008052364 A1 | 5/2008 |

OTHER PUBLICATIONS

Mark H. Beers et al., The Merck Manual of Diagnosis and Therapy 528-31 (17th ed. 1999).*

*Primary Examiner* — Tan-Uyen (Jackie) T Ho
*Assistant Examiner* — Mark K Han
(74) *Attorney, Agent, or Firm* — Price Heneveld LLP

(57) ABSTRACT

A method for administering a gas containing oxygen to a patient. The method includes: measuring an oxygen-dependent physiological parameter in the patient; determining an optimal gas delivery parameter based on the oxygen-dependent physiological parameter; and administering the gas to the patient in accordance with the optimal gas delivery parameter. In some embodiment of the invention, the method also includes monitoring the oxygen-dependent physiological parameter.

5 Claims, 8 Drawing Sheets

(56) References Cited

U.S. PATENT DOCUMENTS

Figure 1:
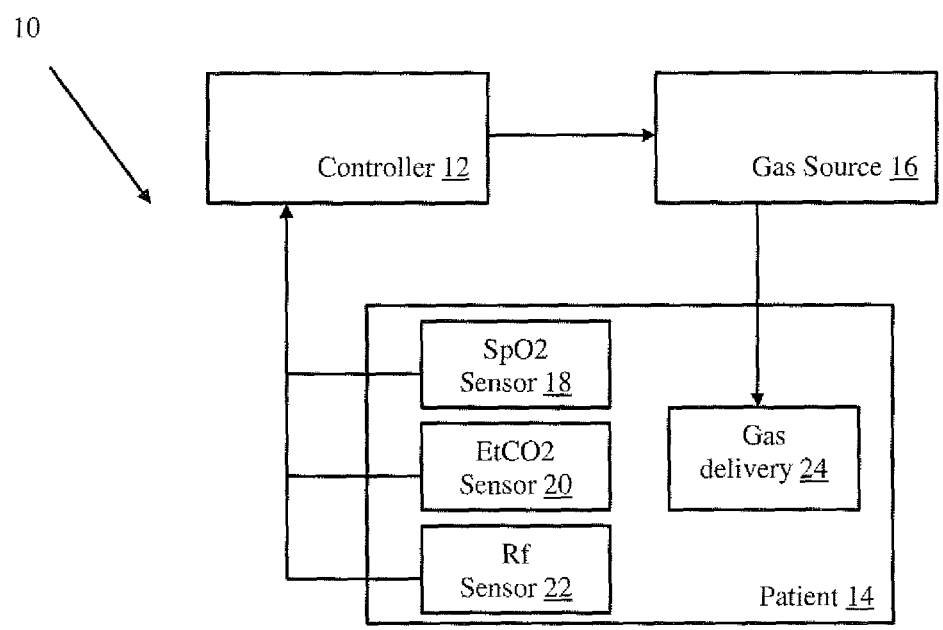

| | | | |
|---|---|---|---|
| 5,365,922 A | 11/1994 | Raemer | |
| 5,495,848 A | 3/1996 | Aylsworth et al. | |
| 5,735,268 A | 4/1998 | Chua et al. | |
| 5,890,490 A | 4/1999 | Aylsworth et al. | |
| 6,142,149 A * | 11/2000 | Steen | 128/204.23 |
| 6,186,142 B1 | 2/2001 | Schmidt et al. | |
| 6,371,114 B1 | 4/2002 | Schmidt et al. | |
| 6,512,938 B2 | 1/2003 | Claure et al. | |
| 6,532,958 B1 * | 3/2003 | Buan et al. | 128/204.23 |
| 6,561,187 B2 | 5/2003 | Schmidt et al. | |
| 6,671,529 B2 | 12/2003 | Claure et al. | |
| 6,675,798 B1 | 1/2004 | Tyomkin et al. | |
| 6,796,305 B1 * | 9/2004 | Banner et al. | 128/204.21 |
| 7,152,604 B2 | 12/2006 | Hickle et al. | |
| 7,222,624 B2 | 5/2007 | Rashad et al. | |
| 7,331,343 B2 | 2/2008 | Schmidt et al. | |
| 7,527,054 B2 | 5/2009 | Misholi | |
| 7,585,351 B2 | 9/2009 | Deane et al. | |
| 2002/0185126 A1 | 12/2002 | Krebs | |
| 2004/0116784 A1 | 6/2004 | Gavish | |
| 2006/0005842 A1 | 1/2006 | Rashad et al. | |
| 2006/0090759 A1 | 5/2006 | Howes et al. | |
| 2006/0124128 A1 | 6/2006 | Deane et al. | |
| 2006/0266355 A1 * | 11/2006 | Misholi | 128/204.23 |
| 2009/0050152 A1 | 2/2009 | Iobbi | |
| 2009/0241956 A1 | 10/2009 | Baker et al. | |
| 2009/0320836 A1 | 12/2009 | Baker | |
| 2010/0094366 A1 * | 4/2010 | McCarthy | 607/3 |
| 2010/0121314 A1 | 5/2010 | Iobbi | |
| 2011/0041850 A1 * | 2/2011 | Vandine et al. | 128/204.23 |

* cited by examiner

METHOD AND DEVICE FOR ADMINISTERING OXYGEN TO A PATIENT AND MONITORING THE PATIENT

This application claims priority from U.S. Provisional Patent Application Ser. No. 61/213,787 filed Jul. 15, 2009, the content of which is hereby incorporated by reference in its entirety.

FIELD OF THE INVENTION

The present invention relates to medical devices and methods. More specifically, the present invention is concerned with a method and device for administering oxygen to a patient and monitoring the patient.

BACKGROUND

Oxygen therapy is used in patients with acute respiratory failure and in other categories of patients without acute respiratory failure, for example for patient with acute myocardial infarction and in post-operative time. Acute respiratory distress is a common cause of hospital admission. During the initial treatment of this clinical situation, the symptomatic treatment plays a major role in reducing complications and improving prognosis. At the forefront of symptomatic treatment is oxygen therapy (OT). OT given to acutely ill people is therefore one of the most common interventions used in modern medicine. However, although the basic principles of OT have been established by painstaking quantitative research over the past 60 years, in practice, most people use oxygen by following customary and generalized practice. When administered correctly, OT may be life saving, but OT is often given without careful evaluation of its potential benefits and side-effects.

Inappropriate dose and failure to monitor treatment can have serious consequences. Omissions and errors are commonly found concerning hospital oxygen use. Oxygen prescription and/or delivery is associated with significantly greater error than that seen with other medications such as antibiotics for example. In several hospital surveys, from 21 to 80% of oxygen prescriptions outside intensive care unit (ICU) environment were determined to be inappropriate in some studies, and 85% of patients were inadequately supervised according to standards. The oxygen dosage is frequently overestimated and frequently underestimated. This poor oxygen prescription rate carries serious potential consequences in both cases.

Another problem that can frequently be observed within units is that OT is not rapidly weaned when no longer required, whereas a clinically stable patient with a certain oxygen flow is considered as "routine". The clinician is often reluctant to decrease the oxygen flow of a stable patient due to the potential risk of subsequent instability. Thus, OT may also induce indirect hospital stay increase, only given the fact that frequent "manual" prescription adaptation may require increases in the staff workload.

In chronic hypoxic patients, survival is improved by long-term OT (LTOT). Such patients often desaturate during activity and at night, despite continuous LTOT administration. Excluding patients with obstructive sleep apnea, episodes of desaturation ($SpO_2 \leq 85\%$) occur during daytime activity and at night during phasic REM sleep in almost $6\pm10\%$ of the time, even under oxygen (continuous flow). These desaturation episodes often remains occult, whereas routine $SpO_2$ monitoring is rarely performed; without automatic adaptation of the oxygen flow to the $SpO_2$ signal, continuous monitoring may in fact be totally inefficient. Survival is known to be worse, at least for patients who desaturate at night.

Against this background, there exists a need in the industry to provide novel methods and devices for improved methods and devices for administering oxygen to a patient and monitoring the patient. An object of the present invention is therefore to provide improved methods and devices for administering oxygen to a patient.

SUMMARY OF THE INVENTION

In a first broad aspect, the invention provides a method for administering a gas containing oxygen to a patient. The method includes: measuring an oxygen-dependent physiological parameter in the patient; determining an optimal gas administration parameter based on the oxygen-dependent physiological parameter; and administering the gas to the patient in accordance with the optimal gas administration parameter.

In some embodiments of the invention, the oxygen-dependent physiological parameter includes an arterial hemoglobin oxygen saturation in the patient. In other embodiments of the invention, the oxygen-dependent physiological parameter includes a pulse oximetry saturation ($SpO_2$) in the patient.

In some embodiments of the invention, the optimal gas administration parameter is selected from the group consisting of a fraction of oxygen in the gas and a flow rate of the gas. In yet other embodiments, both of these parameters are simultaneously determined.

In some embodiments of the invention, an alarm is issued if the oxygen-dependent physiological parameter is measured to be outside of a predetermined interval. Oxygen-dependent physiological parameters that may lead to the issuance of an alarm include, for example, arterial hemoglobin oxygen saturation in the patient, respiratory frequency of the patient and end tidal $CO_2$ level of the patient.

In another broad aspect, the invention provides a system for administering a gas to a patient.

An objective of the proposed method and system is to optimize and monitor the administration of oxygen therapy for a very wide range of clinical settings, from prehospital care to intrahospital care (emergency department, intensive care units, respiratory/cardiology/internal medicine wards, rehabilitation units, post-anesthesia recovering rooms, for example). It is also developed for a use by patients at home for chronic respiratory and cardiac insufficiency. It was developed either for adults or pediatric patients.

Advantageously, the proposed method and system provide improved real-time adjustment of oxygen delivery to the patient at relatively low costs. This real-time adjustment is believed to potentially result in improved prognosis and reduced mortality in a wide range of patients.

In some embodiments of the invention, $SpO_2$, $EtCO_2$, respiratory rate, cardiac frequency and airway pressure are all simultaneously recorded and analyzed to provide a breathing pattern. The controller used in the system is adaptative and automatically adapts to the need of many different patient types and adapts also to the temporal evolution of each patient as the patient heals or deteriorates.

The present document refers to a number of documents, the contents of which are hereby incorporated by reference in their entirety.

Other objects, advantages and features of the present invention will become more apparent upon reading of the following non-restrictive description of preferred embodi-

BRIEF DESCRIPTION FOR DRAWINGS

Figure 2:
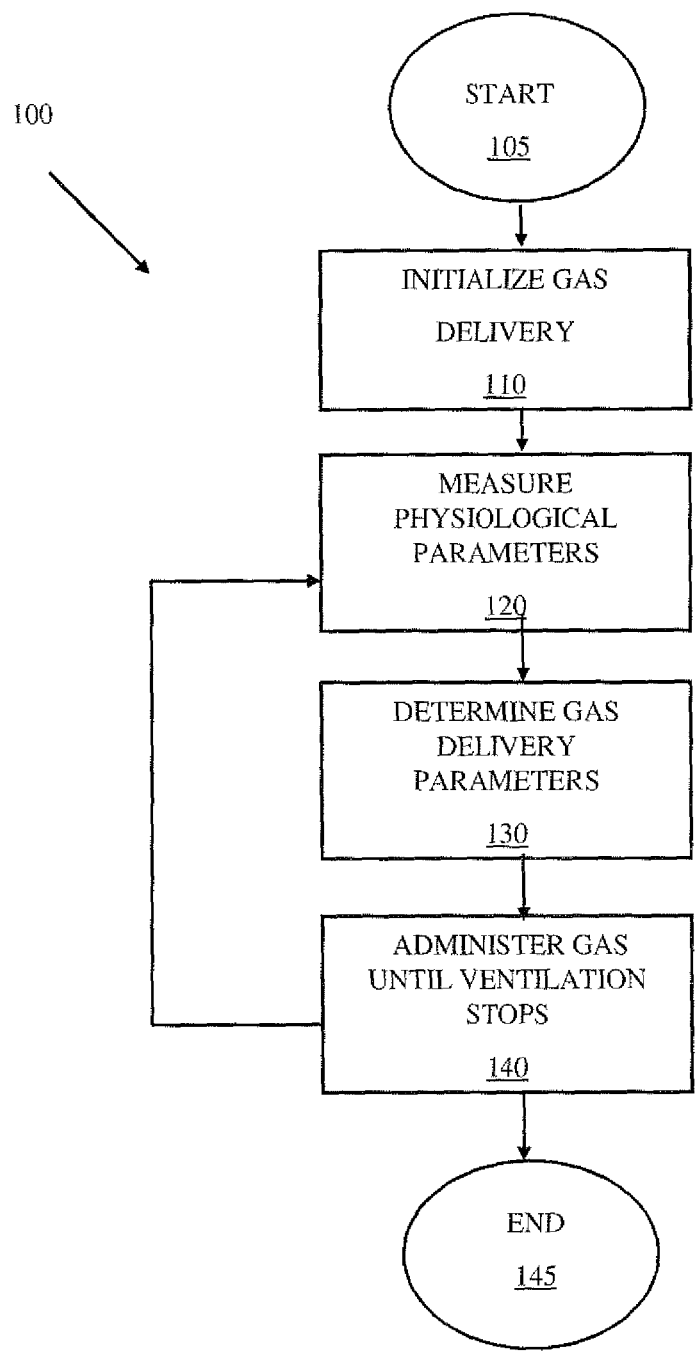
Figure 3:
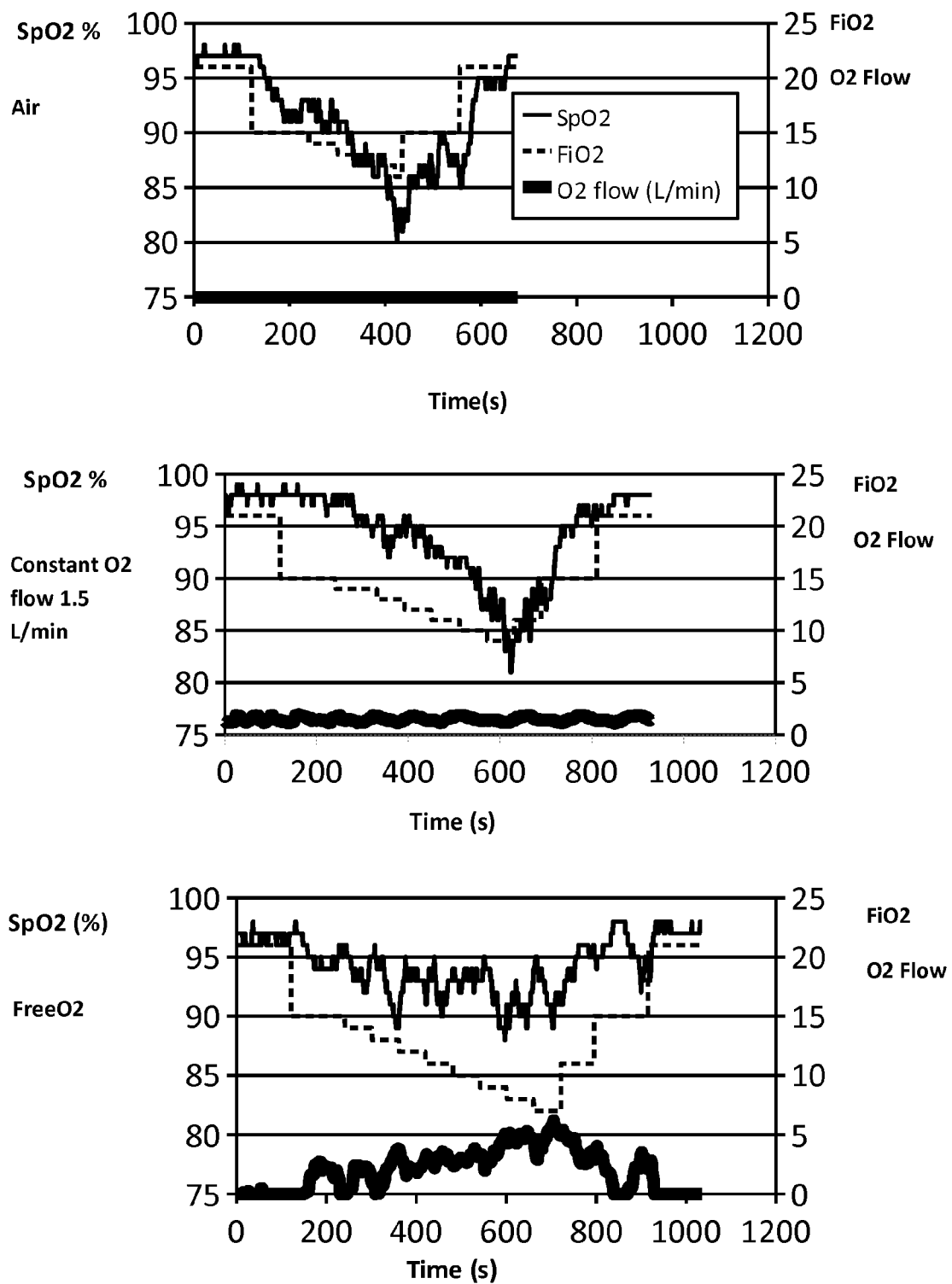
Figure 4:
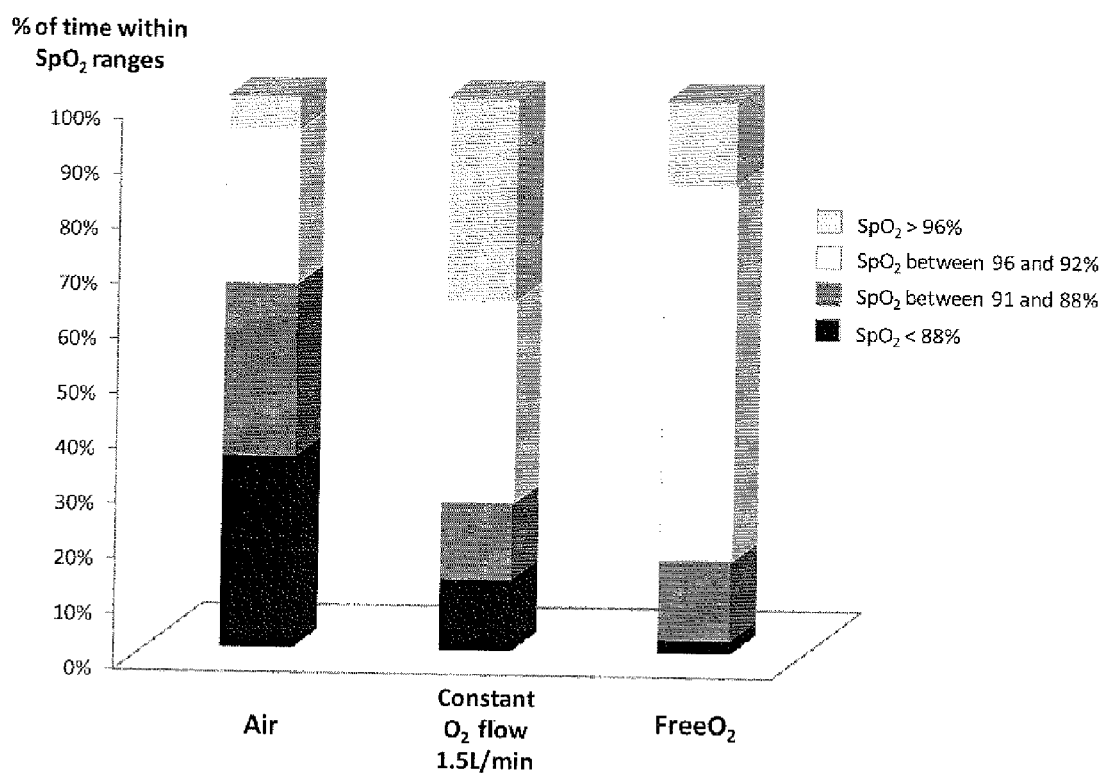
Figure 5:
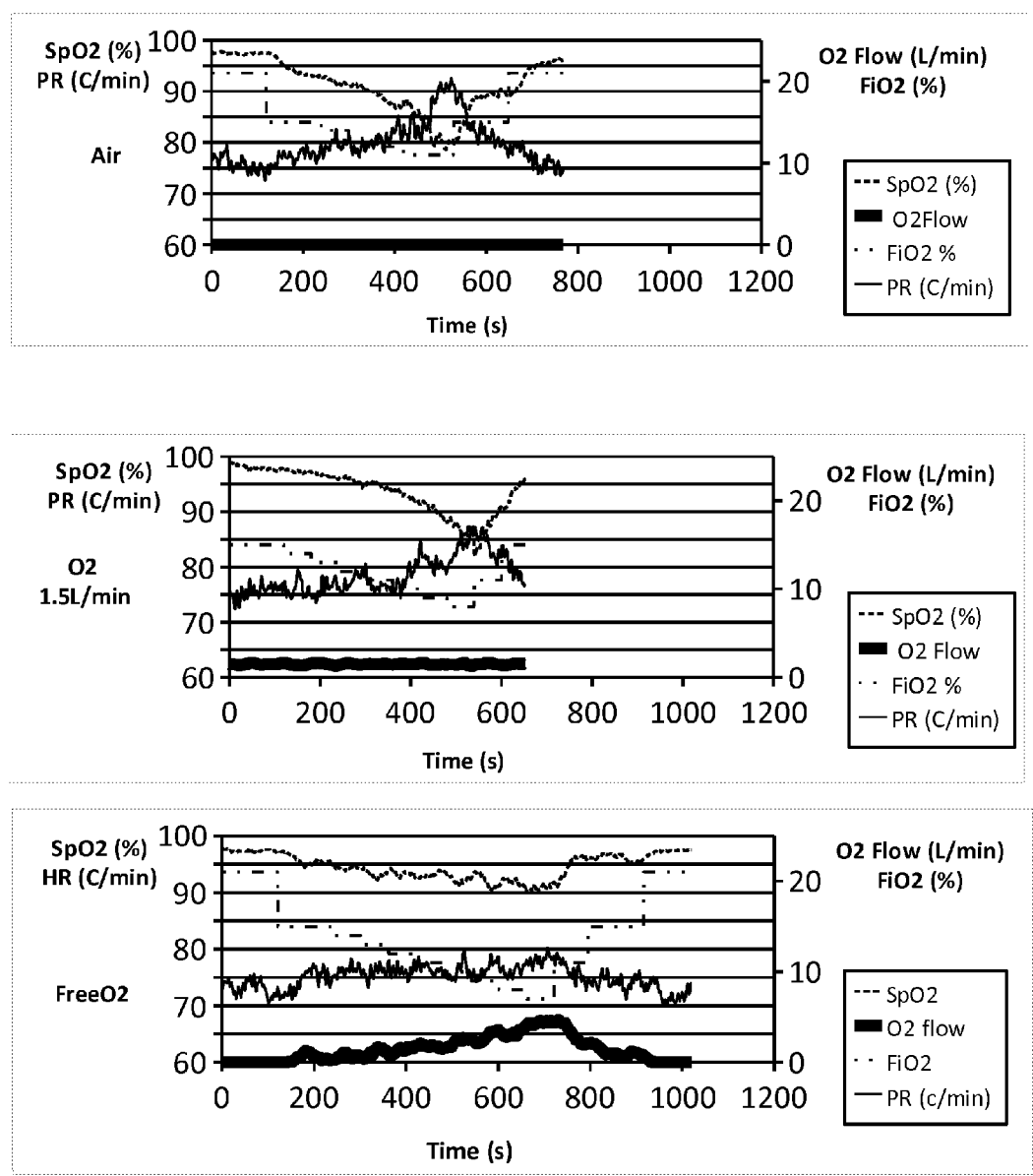
Figure 5A:
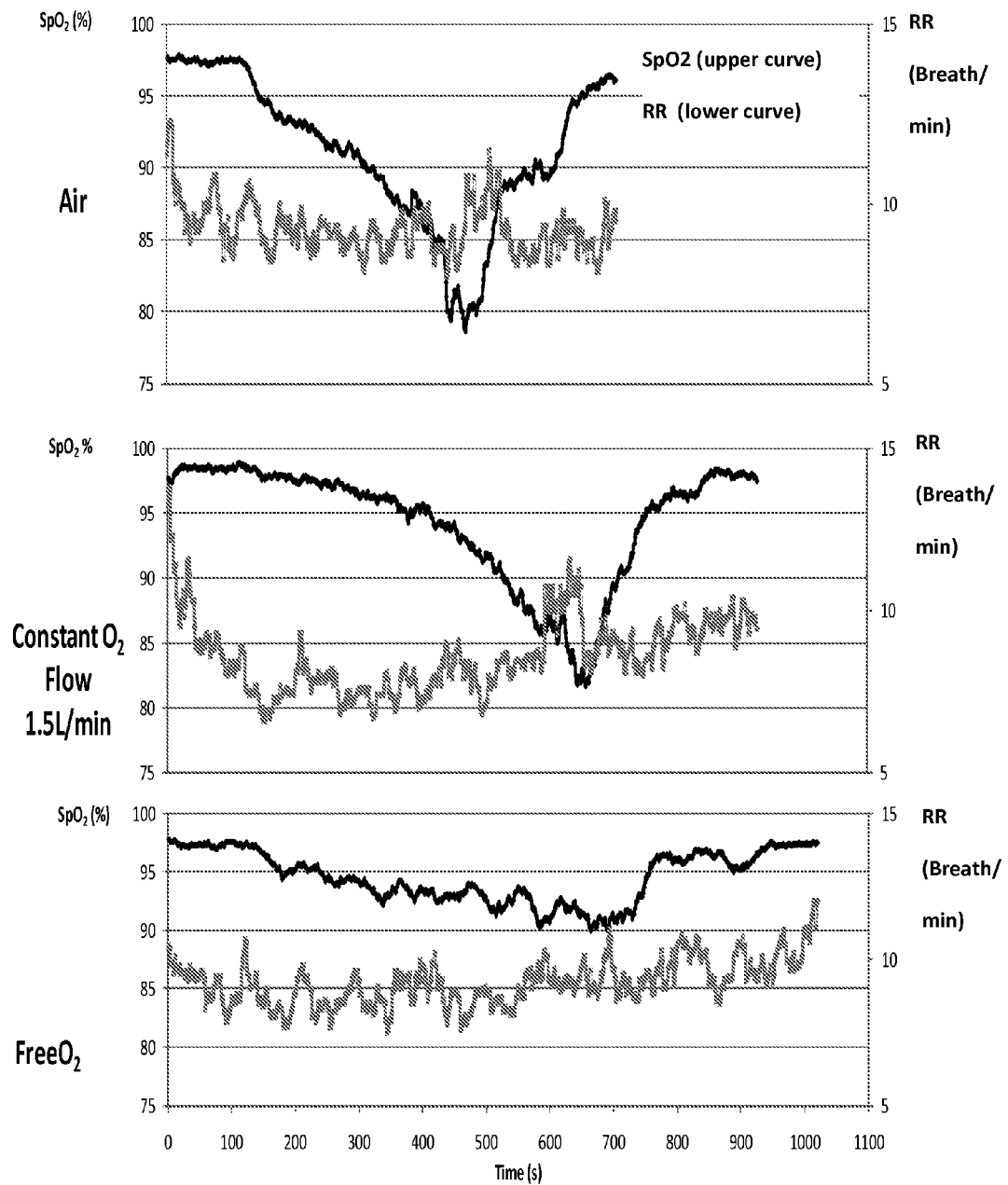

In the appended drawings:

FIG. 1, in a schematic view, illustrates a system for administering a gas to a patient in accordance with an embodiment of the present invention;

FIG. 2, in a flowchart, illustrates method for administering a gas to a patient performed by the system of FIG. 1;

FIG. 3, in X-Y graphs, illustrates a confirmation that the system of FIG. 1 implementing the method of FIG. 2 in a healthy subject can maintain oxygen saturation in artificially induced hypoxia;

FIG. 4, in bar charts, illustrates a confirmation that the system of FIG. 1 implementing the method of FIG. 2 in ten healthy subjects can maintain optimal oxygen saturation in artificially induced hypoxia;

FIG. 5, in averaged X-Y graphs, illustrates a confirmation that the system of FIG. 1 implementing the method of FIG. 2 in ten healthy subjects can maintain oxygen saturation in artificially induced hypoxia;

FIG. 5A, in X-Y graphs, illustrates mean variations of the respiratory rate (RR) during the hypoxemic challenge during the 3 tested conditions illustrated in FIGS. 3 to 5.

Figure 6:
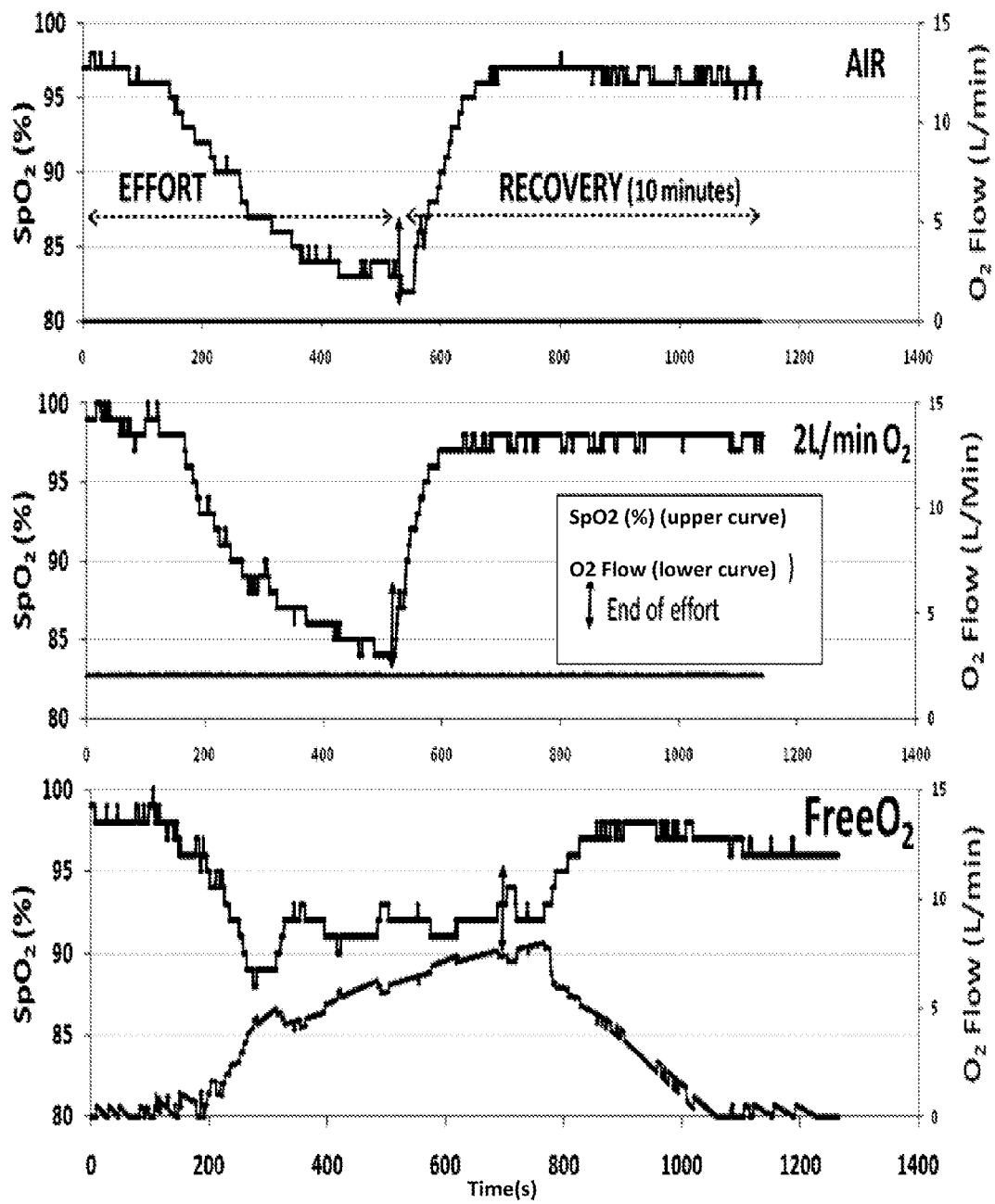

FIG. 6, in X-Y graphs, illustrates SpO2 values (%) and oxygen flow (L/min) during three endurance shuttle walking test (at 85% of the maximal effort) in a COPD patient known to desaturate during effort. Data were recorded during the effort and during 10 minutes of recovery. The tests were conducted with air at a constant flow of 2 L/min (upper graph), with oxygen at a constant flow of 2 L/min (middle graph), and with a variable oxygen flow implemented with the method of FIG. 2. (bottom graph). Desaturation was more severe with air and constant oxygen and duration of effort was reduced in comparison to oxygen administration according to the method of FIG. 2; and FIG. 7, in an X-Y graph, illustrates dyspnea score evaluated every minute with the modified Borg scale during three endurance shuttle walking test (at 85% of the maximal effort) in a COPD patient known to desaturate during effort. Data were recorded during the effort and during 10 minutes for the recovery. End of effort decided by the patient is indicated (with vertically oriented double arrow). The patient experienced a very severe dyspnea (7 on the Borg dyspnea scale) after 7 minutes with oxygen (black line and square), 9 minutes with air (grey line and square) and 11 minutes with the method of FIG. 2 (dotted line and black triangle).

DETAILED DESCRIPTION

FIG. 1 illustrates a system 10 for administering a gas containing oxygen to a patient 14. The system 10 includes a controller 12, a gas source 16 and sensors 18, 20 and 22. The gas source 16 is connected to a gas administration apparatus 24. The gas source 16 is controlled by the controller 12. The controller 12 is connected to the sensors 18, 20 and 22 for receiving signals indicative of physiological parameters measured in the patient. While three sensors 18, 20 and 22 are shown in the drawings, it is within the scope of the invention to use more or less sensors in different embodiments of the invention.

The gas source 16 is usable for providing a gas including oxygen to the patient 14. In some embodiments of the invention, the gas source 16 is an oxygen source providing pure oxygen to the patient. In these embodiments, the controller 12 is usable for controlling a gas flow rate of the gases source 16. In other embodiments of the invention, the gases source 16 provides a mixture of air and oxygen. In these embodiments, the controller 12 is usable for adjusting a fraction of oxygen in the gas and the gas flow rate of the gas source 16. In yet other embodiments of the invention, any other suitable gas source 16 is used. Such gas sources are well known in the art and the gas source 16 will therefore not be described in further details.

The gas administration apparatus 24 is any suitable gas administration apparatus. Examples of such a gas administration apparatus 24 include a venturi mask and eyeglasses provided with gas administration tubes, among other possibilities.

Examples of physiological parameters measured by the sensors 18, 20 and 22 include oxygen-dependent physiological parameters, such as pulse oxymetry oxygen measurement (SpO2), pulse rate, respiratory rate, end tidal $CO_2$ level in the patient and breathing pattern, among other possibilities. In this case, sensor 18 is an oxygen saturometer, sensor 20 is a $CO_2$ concentration sensor and sensor 22 is a respiratory rate sensor. In some embodiments of the invention, the respiratory rate sensor 22 is integrated with the $EtCO_2$ sensor, breathing pattern is derived from pressure measured from $EtCO_2$ sensor and pulse rate is derived from oxymetry (plethysmogram). In some embodiments of the invention, the $EtCO_2$ sensor also allows determination of the airways pressure in the patient 14.

The controller 12 integrates the data conveyed by the sensors 18, 20 and 22, and controls the gas source 16 to deliver the gas to the gas administration apparatus 24 according to optimal gas administration parameters. To that effect, the controller 12 performed a method 100 for administering a gas containing oxygen to the patient 14, shown in FIG. 2.

The method 100 starts at step 105. At step 110, gas administration to the patient 14 is initialized. Afterwards, a loop is made between steps 120, 130 and 140. At step 120, one or more oxygen-dependent physiological parameters in the patient are measured. Then, at step 130, a determination of optimal gas administration parameters based on the oxygen-dependent physiological parameters measured at step 120 is made. Finally, at step 140, administration of the gas to the patient 14 is made in accordance with the optimal gas administration parameters determined at step 130. Afterwards, after a predetermined delay, the method loops back to step 120. This administration is performed until ventilation of the patient 14 stops at which point, the method ends at step 145.

The proposed method 100 is typically performed without mechanically assisted ventilation of the patient 14. However, in alternative embodiments of the invention, such mechanical ventilation is used. As can be understood from the previous paragraph, the proposed method is a closed loop regulation of supplementary oxygen administration.

Initialization of gas administration at step 110 is made in any suitable manner. In a specific embodiment of the invention, this initialization is performed according to the following method:

if pulse oxymetry saturation ($SpO_2$) is larger or equal to 92% (or any other suitable predetermined value), initialization is considered to be completed;

if the patient is younger than a predetermined age, initialization is considered to be completed;

if ($SpO_2$) is smaller than 92% (or any other suitable predetermined value), oxygen administration is raised at a predetermined rate at predetermined time intervals until ($SpO_2$) reaches 92%. This augmentation of oxygen administration is dependent on ($SpO_2$); if this quantity is larger than 90%, in a specific embodiment of the invention, oxygen administration is raised by 0.5 L/min; if this quantity is smaller than 90% but larger than 85%, oxygen administration is raised by 1 L/min; and if this quantity is smaller than 85%, oxygen administration is raised by 2 L/min;

In step 120, physiological parameters of the patient of measured. In some embodiments of the invention, the physiological parameters are averaged to prevent undue variations in their values. Typically, these physiological parameters are oxygen-dependent physiological parameters that are affected by administration of oxygen to the patient. Some of these parameters are used to determine the gas administration parameters at step 130. In some embodiments of the invention, some of the physiological parameters measured are used to issue an alarm if the oxygen dependent physiological parameters are outside of predetermined intervals. Alarms can be issued as text information, sounds, lights or combinations thereof according to conventional alarm issuance methods.

A specific example of alarms that are issued by an embodiment of the controller 12 are as follows:

If oxygen flow rate is larger than or equal to 8 L/min, a message indicating that use of a mask is preferred is issued.

If oxygen flow rate is larger than or equal to 20 L/min and respiratory rate is larger than 30/min, a message indicating that another oxygen administration technique is preferable is issued.

If $SpO_2$ is less than or equal to 85% for more than 3 seconds, a message indicating that connections of the arterial hemoglobin oxygen saturation sensor 18 should be checked is issued and the method 100 steps back to step 110;

If $SpO_2$ is unmeasurable, a message indicating that connections of the arterial hemoglobin oxygen saturation sensor 18 should be checked is issued and the desired oxygen flow rate is set as a minimal safe flow rate, or as the last determined oxygen flow rate.

If $SpO_2$ is larger than or equal to 96% and oxygen flow rate is zero for more than 15 minutes, a message indicating that weaning from oxygen is possible is issued and the method 100 steps back to step 145.

If end tidal $CO_2$ concentration is unmeasurable, a message indicating that connections of the end tidal $CO_2$ concentration sensor 20 should be checked is issued.

If end tidal $CO_2$ concentration is larger than or equal to 45 mmHg or has increased by more than 10 mmHg over the preceding hour, a message indicating the patient 14 should be closely monitored and that another oxygen administration technique may be preferable is issued.

If end tidal $CO_2$ concentration is larger than or equal to 55 mmHg or has increased by more than 20 mmHg over the preceding hour, a message indicating that another oxygen administration technique may be preferable is issued.

At step 130, gas administration parameters are determined. For example, a proportional integral (PI) controller is used. Gas administration parameters are determined in order to maintain one of the measured physiological parameters within a predetermined interval or as close as possible to a target value. In a specific embodiment of the invention, the measured physiological parameter is indicative of $SpO_2$ in the patient and a target value of, for example, 94% saturation is selected. This target value can be adjusted according to the patient 14 in accordance with conventional criteria.

In another specific embodiment of the invention, the measured physiological parameter is indicative of end tidal $CO_2$ concentration in the patient and a target value of, for example, 40 mmHg is selected. This target value can be adjusted according to the patient 14 in accordance with conventional criteria.

In yet another specific embodiment of the invention, the measured physiological parameter is the respiratory rate of the patient and a target value of, for example, less than 30/min is selected. This target value can be adjusted according to the patient 14 in accordance with conventional criteria.

At step 140, the gas source 16 is operated so that the gas is administered to the patient in accordance with the optimal gas administration parameters determined at step 130. This is typically performed by regulating the flow of the gas from one or more valve in the gas source 16.

In summary, the proposed system 10 is a closed-loop system allowing the automatic adjustment of fractional oxygen content and/or gas flow of a gas according to three different and concomitant physiological parameters evaluation, the arterial hemoglobin oxygen saturation, obtained for example by pulse oximetry ($SpO_2$), a parameter indicative of $CO_2$ content in the blood of the patient, either through the pressure of transcutaneous $CO_2$ ($PtcCO_2$) or the end tidal $CO_2$ concentration ($EtCO_2$), and the respiratory rate (RR), based on the transfer of clinical knowledge and the automatic application of rules.

In some embodiments of the invention, the above described method is used until the physiological parameters for the patient are within a predetermined interval relative to target values. Then, an adaptative or a non-adaptative PID controller set at the target values is used to adjust the gas source 16. For example, the adaptative PID controller is used when the $SPO_2$ measured in the patient is within 2 percent of the target $SPO_2$. Also, other controllers can be used in this situation, for example PI controllers, among other possibilities. In some embodiments, the setpoint is determined by medical studies and knowledge, and the process controlled by the controller is the patient 14. The measured and controlled output are respectively the $SpO_2$ and the blood oxygen saturation. Through many studies, a model is generated to predict the patient's response to various levels of oxygen administered, and based on that model, the parameters of the controller are determined. In other embodiments, when the controller is adaptative, the response of the patient 14 to the treatment is used to adjust the parameters of the controller. In yet other embodiments, the parameters of the controller are determined for the patient using a calibration routine.

Examples of potential applications of the system 10 are: emergency and intensive care in patients with hypoxemia (pneumonia, cardiogenic pulmonary edema, acute chronic obstructive pulmonary disease (COPD) exacerbations . . . etc. . . . ), in intensive care for patients with the most severe hypoxemia cases; respiratory failure related to pandemia; in the anesthesia recovery room for the monitoring of hypercapnia risk in awakening patients, pulmonology and general wards for all patients under oxygen (in such ward the ratio nurse/patient is low and thus monitoring and prescription adaptation is quite deficient), rehabilitation for patients with pulmonary insufficiency or cardiac failure, at home OT for chronic respiratory insufficient patients in long-term oxygen therapy, cardiology ward for the rehabilitation effort of the heart failure or patients with myocardial infarction, among others.

The system 10 may also be provided with monitoring and diagnostic capabilities. For example, the system 10 may be provided with a microcomputer that may store continuously all the data provided by the sensors 18, 20 and 22. The data thus collected can be reviewed by a physician either upon the patient visiting the physician, or by remotely accessing the data contained in the microcomputer. This would allow immediate evaluation of treatment efficiency, clinical stability of the patient and evaluation of optimal oxygen delivery parameters as a function of patient physical activity.

The time evolution of the data recorded can alert the physician if the patient is deteriorating, for example if heart rate, respiratory rate or oxygen consumption increases. In some embodiments, this diagnostic capability is increased by a correlation between the data pertaining to different sensors 18, 20 and 22.

Advantageously, as demonstrated in the examples found hereinbelow, the proposed system can optimize the time spent in the optimal $SPO_2$ interval while minimizing the mean oxygen flow rate, allowing therefore a substantial reduction in oxygen consumption.

This reduction is advantageous for many patient types. First, for ambulatory patients, patient autonomy is improved. Also, for all patients, the reduction in oxygen consumption greatly reduces treatment cost and increases the number of patients that can be treated in remote regions or during emergency situations in which oxygen supplies are limited.

Furthermore, the system 10 and the method 100 are usable both for low and high oxygen flow rates, which provides a wide range of clinical situations in which they can be used.

Example 1

The system 10 and the implementation of the method 100 have been investigated in healthy subject in which hypoxemia and hypercapnia have been simulated. Healthy subjects were free of cardiac or respiratory conditions, as well as epilepsy or any other chronic pathology requiring drug treatment. Also, pregnant women were excluded from the study.

To simulate various conditions, nitrogen enriched air or $CO_2$ enriched air has been administered using a mask in order to obtain respectively an arterial hemoglobin oxygen saturation between 84% and 86% and an end tidal $CO_2$ between 50 and 55 mmHg.

Hypoxemia studies were performed under three conditions: using only air, using a constant flow rate of oxygen added to air, and using the system 10, all 3 performed in a randomized order blind to the patient only. A progressive lowering of oxygen content of the gas from 21% to 7% was performed in all three cases, unless oxygen saturation fell below 84%, in which case the experiment was stopped and oxygen content was raised gradually. During these experiments, three conditions have been compared, namely without additional oxygen, using the system 10, and using an additional 1.5 L/min of oxygen. Table 1 summarizes the results of these experiments.

Results for one of the subjects are shown in FIG. 3. In all three panels, the step-like and dotted curve represents oxygen concentration in the air provided to the patient, the lower curve represents oxygen flow rate and the last, jagged, curve, represents arterial hemoglobin oxygen saturation. As seen in the upper panel, when no supplemental oxygen is administered the patient, oxygen saturation in the blood decreases gradually as oxygen content in the gas breath by the subject is reduced. As shown in the middle panel, with the constant flow rate of oxygen of 1.5 L/min, oxygen saturation in blood still decreases but is delayed when compared to the curves of the upper panel. Using the system 10, as seen in the lower panel, oxygen saturation remains within the target region and oxygen flow rate increases gradually as required.

FIG. 4 shows for the three experiments described above in the same order as the order of description in FIG. 3 the relative duration of various zones of oxygen saturation. It is desirable that a maximum amount of time is spent in the target oxygen saturation region represented by the dark green curves in FIG. 4. Only the system 10 provides for optimal oxygen saturation with about 70% of time spent within the 92-96% saturation target region (lightest shade) and almost no time spent in severe oxygen desaturation (darkest shade).

FIG. 5 shows results similar to the data of FIG. 3 averaged for 10 subjects. Ten healthy subjects were included in the study (7 women/3 men). Mean age was 25.5±5.5 years, and mean body mass index was 24.7±4.0 Kg/m2. All the subjects completed the study. Results of substantially similar to the results of FIG. 3. In addition, heart rate data is presented (thinnest curve). The system 10, in addition to preventing oxygen desaturation, also prevents tachycardia due to lack of oxygen. FIG. 5A illustrates the effect of the various experiments on the respiratory rate of the subject.

The above results demonstrate that with the system 10: (i) the predefined oxygenation target (92% SpO2 96%) was significantly better maintained (ii) severe desaturations (SpO2<88%) were significantly less frequent (iii) periods with hyperoxia (SpO2 97%) were significantly decreased (iv) and episodes of tachycardia were significantly less in comparison with air or constant oxygen flow. Also, these results were obtained with 15% less oxygen consumption, in comparison with a constant oxygen flow.

Example 2

The system 10 and the implementation of the method 100 have been investigated in a COPD patient, exhibiting $O_2$ desaturation during exertion. The patient signed an informed consent before the study. Five visits were performed with a minimum of 48 hours between each visit. The first visit was intended to perform an incremental shuttle walking test (ISWT). During the second visit, the patient was trained to perform an endurance shuttle walking test (ESWT) at an intensity representing 85% of the peak $VO_2$ as predicted from the ISWT. At visits #3, 4 and 5, one ESWT was performed in a blinded and random order with one of the following conditions: (i) air at a fixed flow of 2 L/min (ii) oxygen at a fixed flow of 2 L/min (iii) the system 10 (variable oxygen flow). The ESWT was followed by a 10-minutes recovery period. Before each endurance test, patients were asked to walk or cycle for as long as possible. No encouragement was provided during the tests to avoid any potential confounding effect on exercise performance. The endurance shuttle walk was performed in a corridor on a flat 10-m-long course, as previously described in Singh, S. J., et al., *Development of a shuttle walking test of disability in patients with chronic airways obstruction*. Thorax, 1992. 47(12): p. 1019-24. and in Revill, S. M., et al., *The endurance shuttle walk: a new field test for the assessment of endurance capacity in chronic obstructive pulmonary disease*. Thorax, 1999. 54(3): p. 213-22. In addition, the effort tolerance was assessed, based on the modified 10-points Borg scale as well as the effort duration were sampled at the end of each effort and at the end of the recovery time.

Figure 7:
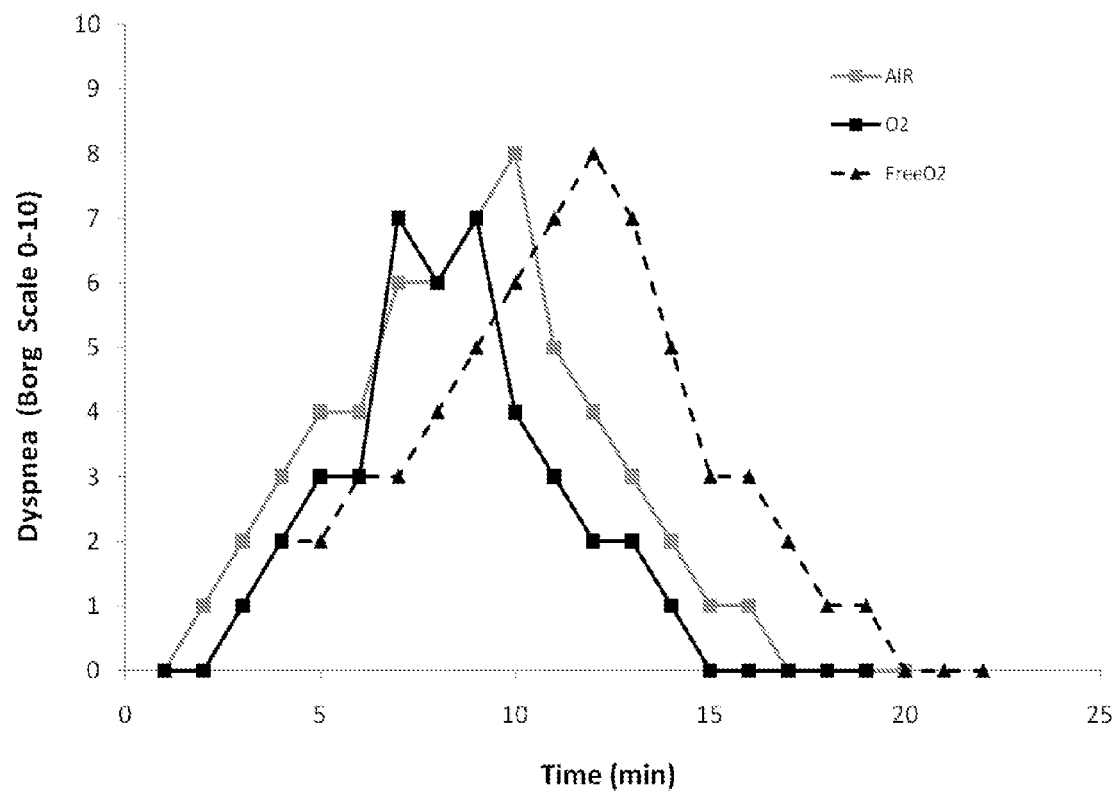

Patterns similar to those of the above-described results in healthy subjects were observed in the 50 years old COPD patient with FEV1 at 1170 ml (43% of the predicted value) previously known to desaturate during exertion. Time within the $SpO_2$ target (92-96%) was higher with the system 10 (48.7%), in comparison with air (34.0%) and constant oxygen (9.4%). No severe desaturation ($SpO_2$ below 88%) occurred with the system 10, as compared with 26.7 and 18.6% of the time with air and constant oxygen. Hyperoxia (SpO2>97%)

was less frequent with the system 10 (19.1%) in comparison with constant oxygen (47.7%). With the system 10, effort tolerance was increased with higher duration of the ESWT and reduced dyspnea in comparison with air and constant oxygen flow. Mean and maximal oxygen flows with the system 10 were 3.3 and 8.0 L/min respectively. FIGS. 6 and 7 and Table 2 summarize the results of these experiments.

Analysis of Examples 1 and 2

This study is the first evaluation of the system 10 that automatically adapts the oxygen flow in closed-loop with SpO2 signal in spontaneously breathing subjects. In this specific model, the automated adaptation of the oxygen flow is proved to be feasible and several advantages are demonstrated in comparison with the constant oxygen flow or air.

Increase of the Percentage of Time within the Oxygenation Target.

The main outcome criterion was to keep the subjects within a predetermined SpO2 range. In the daily practice, the oxygen flow is either fixed (most of the time in patients with LTOT) or manually adjusted (in the hospital setting). The $SpO_2$ range (higher and lower limit) is not clearly defined. A commonly accepted aim of Long Term Oxygen Therapy (LTOT) is to maintain COPD patients with $SpO_2$ above 90%. In patients without $CO_2$ retention, the minimum recommended $SpO_2$ level is 92%. The upper $SpO_2$ limit is not clearly defined. We choose to define the $SpO_2$ upper limit at 96%, considering the potential risks associated with hyperoxia, and the uselessness to maintain high $SpO_2$ (with the possible exception of patients after abdominal surgery). The same target (92-96%) was also chosen in two studies evaluating closed loop devices adjusting the $FiO_2$ in intubated patients.

Reduction of Severe Oxygen Desaturations

With automated adjustment of the oxygen flow, the frequency of severe oxygen desaturations ($SpO_2$ below 88%) was very low (0.4%) in comparison with constant oxygen flow (12.7%) and with air (33.7%). The median minimal $SpO_2$ values were respectively 86.5, 79 and 76.5%. The reduction of the desaturation frequency and depth may have a clinical impact in various clinical settings.

In patients with COPD, long term oxygen therapy has benefits with mortality reduction. However, even with oxygen supplementation, desaturations still frequently occur during the night as well as during daily activities. Some data suggests that even short periods of hypoxemia may promote adverse effects. A study demonstrated that pulmonary artery pressure and pulmonary vascular resistance significantly increased within 2.5 h after the removal of oxygen supplementation in COPD patients. In an animal model, it was also shown that right ventricular hypertrophy can occur with as little as 2 h of hypoxemia per day. Risks associated with oxygen desaturations are also well known in premature infants with neurological deficiencies, as well as aggravation of prematurity retinopathy induced by hyperoxia. The temporal link between hypoxemia and tachycardia/myocardial ischemia has also been well demonstrated in patients with coronary artery disease. After abdominal surgery, hypoxemia occurs frequently with associated risks of tachycardia and myocardial ischemia. In patients with brain injury, hypoxemia increases morbidity and morbidity and is considered as a secondary insult. In our study, severe desaturations were virtually absent with the system 10 (as compared to 13% of the time with constant oxygen flow and 34% without oxygen (table 1). In the COPD patients, the reduction of severe desaturations may improve LTOT efficacy. Reduction of desaturation may also improve exercise tolerance in COPD patients. In the acute setting, cardiac complications in patients with coronary artery disease, worsening of the neurologic condition in patients with trauma and complications related to hypoxemia in preterm infants may be reduced by reducing severe desaturation frequency.

Prevention of Hyperoxia

On the other side, excessive oxygen flow leading to hyperoxia may have deleterious effects in different populations. It has been shown that hyperoxia causes a significant reduction in coronary artery blood flow, with increase of the coronary artery resistances. High oxygen flows in patients with myocardial infarction may therefore be deleterious. In a randomized controlled double blind study comparing oxygen to air administered at 6 L/min in patients with acute myocardial infarction, 9/80 (11.3%) deaths occurred in the oxygen group, as compared to 3/77 (3.9%) in the air group, with a relative risk of death 2.9 (95% CI 0.8 to 10.3, p=0.08). Hyperoxia may also be responsible of cerebral artery vasoconstriction, and in low birth weight infants, it is well demonstrated that hyperoxia is a contributing factor for the retinopathy of prematurity. In the present study, the median percentage of time with hyperoxia (SpO2 97%) was 14.5% with automatic adjustment of the oxygen flow, as compared to 39.1% under constant oxygen (table 1).

Impact on Tachycardia

Tachycardia induced by hypoxemia has been well described in several physiological studies. In one study, episodes of oxygen desaturation in COPD patients was associated with a marked increase of the pulse rate during activity, as well as during rest. In chronic respiratory failure patients, tachycardia induced by hypoxemia is more significant than in healthy subjects. Oxygen desaturation is also associated with tachycardia and myocardial ischemia in patients with coronary artery diseases. In this type of patients, cardiac adverse events may be induced by increased oxygen consumption related to tachycardia. Also, it is well recognized that tachycardia increased cardio-vascular morbidity and mortality. In the present study, oxygen desaturation was associated with severe tachycardia in healthy subjects. Tachycardia occurred with constant oxygen and with air, but not with the system 10.

Impact on Tachypnea

In healthy subjects, initial response to hypoxia is an increase of the tidal volumes and the impact on the respiratory rate is less. On the contrary, in COPD patients with reduced ventilatory reserve, hypoxia leads to both increase of the respiratory rate and of the tidal volumes [56]. In the present study conducted in healthy subjects, respiratory rate was slightly increased during desaturation but this effect, though statistically different, was not clinically relevant.

Other Potential Advantages of Automated Adjustment of Oxygen Flow

In our study, the beneficial effects (maintain in the oxygenation target, reduction of severe desaturation, reduction of hyperoxia) were obtained with reduced oxygen consumption, as compared to constant oxygen flow (table 1). The reduction of the oxygen consumption may be interesting in patients under LTOC. During medical transportation, minimizing of oxygen consumption may also be of great importance, while it may increase gas autonomy in situations of restrained resources. Another advantage of such a system is the possibility to provide to the clinicians a continuous monitoring of the respiratory pattern, including $SpO_2$, $EtCO_2$, respiratory rate, oxygen needs, as well as an evaluation of minute ventilation. Current memory capacities of the controller allows recording of these parameters every second during several months.

Example 3

Five COPD patients were studied in accordance with a protocol similar to that of Example 2. Inclusion criteria were the following: age >40 years, moderate to very severe COPD with known desaturation during exertion (or suspected if SpO2 at rest is below 95%), smoker or ex-smoker. Five visits were planned with a minimum of 48 hours between each visit. At study visits #1, 2 and 3, one ESWT is performed in a random order with one of the following conditions: 1) air at 2 L/min 2) oxygen at 2 L/min 3) using the system 10 (variable oxygen flow: SpO2 target set at 94%). Patient date is shown in table 3.

Results, shown in table 4, were qualitatively similar to those of example 2 with a near doubling of the walking distance when the system 10 is used as compared to the other two protocols. More information is found in Lellouche, F., et al., *FreeO$_2$: closed-loop automatic titration of oxygen flow based on SpO$_2$. Evaluation in COPD patients during endurance shuttle walking.* Am J Respir Crit Care Med, 2010. 181: p. A6785.

Although the present invention has been described hereinabove by way of preferred embodiments thereof, it can be modified, without departing from the spirit and nature of the subject invention as defined in the appended claims.

TABLE 1

Impact of oxygen administration on SpO$_2$, pulse rate and respiratory rate during the hypoxemic challenge.

|  | Air | Constant oxygen (1.5 L/min) | Variable flow (FreeO$_2$) | P value |
|---|---|---|---|---|
| % of time with SpO$_2$ > 96% | 4.1 (2.1-7.6) | 39.1 (25.1-43.2) | 14.5 (8.6-19.0) | <0.001 |
| % of time with SpO$_2$ 92-96% | 26.0 (23.1-27.5) | 36.8 (31.0-43.4) | 66.5 (63.5-74.1) | <0.001 |
| % of time with SpO$_2$ 91-88% | 33.3 (22.6-36.9) | 14.6 (12.6-16.5) | 16.6 (11.2-17.4) | <0.001 |
| % of time with SpO$_2$ < 88% | 33.7 (30.6-40.7) | 12.7 (10.0-14.0) | 0.4 (0.00-5.2) | <0.001 |
| Minimum SpO$_2$ (%) | 76.5 (75.3-78.8) | 79 (78.3-81.0) | 86.5 (84.3-87.8) | 0.003 |
| Minimum FiO$_2$ step completed (%) | 11 (10.3-12.0) | 8 (8-9) | 7 (7-7) | <0.001 |
| Pulse rate (/min) | | | | |
| Median (25-75th) | 80 (77-83) | 77 (76-80) | 75 (74-77) | 0.024 |
| min-max | 69-93 | 71-91 | 70-80 | 0.082* |
| delta | 24 | 21 | 10 | 0.031 |
| Respiratory rate (breath/min) | | | | |
| Median (25-75th) | 9.0 (7.8-10.3) | 8.1 (6.9-9.7) | 8.8 (8.1-10.1) | 0.79 |
| min-max | 6-16.1 | 4.9-17.3 | 5.4-17.5 | |
| delta | 10.1 | 12.4 | 12.1 | 0.11 |
| Median oxygen flows | 0 | 1.5 | 1.0 (0-2.6) | |
| Maximum oxygen flows | 0 | 1.5 | 5.8 (5.6-6.6) | |

TABLE 2

Main results for the clinical evaluation: COPD patient during exertion with air during endurance shuttle walking test with air, constant oxygen or with the system 10, referred to as FreeO$_2$.

|  | Minimum SpO$_2$ (%) | % of time with SpO$_2$ < 88% | % of time with SpO$_2$ < 90% | % of time with SpO$_2$ > 96% | % of time with SpO$_2$ 92-96% | Duration of the effort |
|---|---|---|---|---|---|---|
| AIR (2 L/min) | 82 | 26.7 | 29.5 | 1.1 | 34.0 | 8 min 54 sec |
| O$_2$ (2 L/min) | 84 | 18.6 | 23.8 | 47.7 | 9.4 | 9 min 01 sec |
| FreeO$_2$ | 88 | 0.0 | 3.9 | 19.1 | 48.7 | 11 min 35 sec |

TABLE 3

Main characteristics of COPD patients who completed the study of example 3.

| Patient # | Age (years) | Sex | BMI | FEV1 (L) | FEV1 (% pred.) | FEV1/FCV (%) | pH | PaCO$_2$ (mmHg) | HCO$_3$— (meq/L) | PaO$_2$ (mmHg) | SaO$_2$ (%) | VO$_2$ peak (mL/kg/min) |
|---|---|---|---|---|---|---|---|---|---|---|---|---|
| 1 | 60 | H | 21.6 | 1.2 | 43 | 38 | 7.40 | 40.5 | 24.9 | 78.3 | 95 | 22 |
| 3 | 75 | H | 30.9 | 1.2 | 50 | 43 | 7.42 | 39.9 | 25.4 | 64.9 | 92 | 16 |
| 4 | 69 | H | 25.1 | 1.8 | 68 | 50 | 7.45 | 35.2 | 25.2 | 87.0 | 97 | 10 |
| 5 | 67 | F | 22.0 | 1.1 | 56 | 40 | 7.41 | 36.2 | 23.3 | 59.8 | 91 | 19 |
| Mean | 67.8 |  | 24.4 | 1.3 | 54 | 43 | 7.42 | 38.0 | 24.7 | 72.5 | 94 | 17 |
| SD | 6.2 |  | 3.9 | 0.3 | 11 | 5 | 0.02 | 2.6 | 1.0 | 12.4 | 3 | 5 |

TABLE 4

Main results of COPD patients who completed the study of example 3. Main results. Minimum, mean SpO₂ and % of time within different SpO₂ ranges. Endurance time and walking distance. Comparison of the ESWT performed with air, with constant oxygen (2 L/min) and with the system 10 (FreeO₂).

| | Mean SpO$_2$ (%) | Mean SpO$_2$ effort (%) | Min SpO$_2$ (%) | % of time SpO$_2$ > 96 | % of time SpO$_2$ 92-96 | % of time SpO$_2$ 88-91 | % of time SpO$_2$ < 88 | Endurance time (s) | Walking distance (m) |
|---|---|---|---|---|---|---|---|---|---|
| AIR | 87.3 ± 4.6 | 83.8 ± 5.6 | 77.7 ± 4.0 | 10.0 ± 17.2 | 20.1 ± 15.7 | 21.7 ± 14.2 | 48.6 ± 18.4 | 663 ± 124 | 640 ± 100 |
| Constant O$_2$ | 90.4 ± 4.3 | 86.8 ± 5.3 | 81.0 ± 4.3 | 23.6 ± 30.0 | 30.2 ± 14.0 | 12.0 ± 4.1 | 34.2 ± 19.4 | 580 ± 102 | 600 ± 126 |
| FreeO$_2$ | 93.3 ± 1.0 | 91.8 ± 1.3 | 88.8 ± 1.5 | 17.1 ± 10.2 | 50.3 ± 23.2 | 30.2 ± 20.0 | 0.7 ± 0.9 | 1068 ± 315 | 1180 ± 510 |

What is claimed is:

1. A method for administering a gas containing oxygen to a patient with hypoxemia or hypoxia, said method comprising:
    (a) providing an age of said patient;
    (b) determining a predetermined patient age;
    (c) providing a predetermined pulse oxymetry saturation threshold of about 92% or about 94%;
    (d) if the patient's age is greater than or equal to the predetermined patient age, carrying out a closed-loop initialization step comprising:
        measuring a pulse oxymetry saturation in said patient;
        comparing the measured pulse oxymetry saturation to the predetermined pulse oxymetry saturation threshold;
        if the measured pulse oxymetry saturation is below the predetermined pulse oxymetry saturation threshold, administering a gradually increasing flowrate of the gas containing oxygen to the patient using a controller;
        if the measured pulse oxymetry saturation is greater than or equal to the predetermined pulse oxymetry saturation threshold, exiting the closed-loop initialization step;
    (e) if the patient's age is lower than the predetermined age or if the measured pulse oxymetry saturation is greater than or equal to the predetermined pulse oxymetry saturation threshold, performing a closed-loop control step comprising:
        measuring the pulse oxymetry saturation in said patient;
        if the measured pulse oxymetry saturation is below about 85% for a period of time longer than about 3 seconds, generating an alarm and reinitiating the closed-loop initialization step;
        otherwise, determining an optimal gas administration parameter based on said measured pulse oxymetry saturation, and administering said gas to said patient in accordance with said optimal gas administration parameter.

2. The method as claimed in claim 1, wherein said gas is pure oxygen and said optimal gas administration parameter is an optimal oxygen flowrate, the closed-loop control step further comprising the step of:
    issuing a message indicating that a mask should be used if said optimal oxygen flowrate is above or equal to 8 liter/min.

3. The method as claimed in claim 1, wherein said gas is pure oxygen and said optimal gas administration parameter is an optimal oxygen flowrate, the closed-loop control step further comprising the steps of:
    measuring a respiratory rate in said patient;
    issuing a message indicating that another oxygen administration technique should be used if said optimal oxygen flowrate is above or equal to 20 liter/min and the measured respiratory rate is above 30 respirations per minute.

4. The method as claimed in claim 1, wherein generating the alarm comprises issuing a message indicating checking connections of an arterial hemoglobin oxygen saturation sensor.

5. A method for administering a gas containing oxygen to a patient with hypoxemia or hypoxia, said method comprising:
    (a) acquiring an age of said patient;
    (b) providing a predetermined patient age;
    (c) providing a predetermined pulse oxymetry saturation threshold of about 92% or about 94%;
    (d) administering the gas at a first gas administration flowrate to the patient;
    (e) measuring a pulse oxymetry saturation in said patient;
    (f) if the measured pulse oxymetry saturation is below a predetermined pulse oxymetry saturation threshold and said patient's age is greater than or equal to the predetermined patient age, carrying out an initialization method comprising the steps of:
        determining a gas administration increase rate based on the measured pulse oxymetry saturation;
        increasing the administered gas flowrate by the determined gas administration increase rate and returning to step (e); and
    (g) if the measured pulse oxymetry saturation is above or equal to the predetermined pulse oxymetry saturation threshold or if said patient age is lower than the predetermined age, performing a closed-loop control method including:
        adjusting the administered gas flowrate based on the measured pulse oxymetry saturation, using one of a proportional integral controller and a proportional integral derivative controller;
        measuring the pulse oxymetry saturation in said patient; and
        if the measured pulse oxymetry saturation is below 85% for a period of time longer than about 3 seconds, generating an alarm and re-initiating the initialization method.

* * * * *